US006172096B1

(12) United States Patent
Gregory et al.

(10) Patent No.: US 6,172,096 B1
(45) Date of Patent: Jan. 9, 2001

(54) IMMUNOSUPPRESSIVE EFFECTS OF ADMINISTRATION OF A CYCLOOXYGENASE-2 INHIBITOR AND A LEUKOTRIENE B⁴ RECEPTOR ANTAGONIST

(75) Inventors: Susan A Gregory, St. Louis; Peter C Isakson, Clarkson Valley; Gary Anderson, Maryland Heights, all of MO (US)

(73) Assignee: G. D. Searle & Co., Chicago, IL (US)

( * ) Notice: Under 35 U.S.C. 154(b), the term of this patent shall be extended for 0 days.

(21) Appl. No.: 09/075,633

(22) Filed: May 11, 1998

Related U.S. Application Data

(63) Continuation of application No. 08/600,580, filed on Feb. 13, 1996.

(51) Int. Cl.⁷ ................... A61K 31/415; C07D 231/02; C07D 231/12
(52) U.S. Cl. ................. 514/395; 514/406; 548/370.1; 548/377.1; 548/364.1; 548/365.7
(58) Field of Search ............... 548/370.1, 377.1, 548/364.1, 365.7; 514/406, 395

(56) References Cited

U.S. PATENT DOCUMENTS

| 4,595,699 | 6/1986 | Terada et al. . |
| 5,246,965 | 9/1993 | Main . |
| 5,344,991 | 9/1994 | Reitz et al. . |
| 5,380,738 | 1/1995 | Norman et al. . |
| 5,384,318 | 1/1995 | Eggler et al. . |
| 5,393,790 | 2/1995 | Reitz et al. . |
| 5,700,816 | * 12/1997 | Isakson et al. ............... 514/406 |

FOREIGN PATENT DOCUMENTS

| 4228201 | 3/1994 | (DE) . |
| 94/02448 | 2/1994 | (WO) . |
| 94/13635 | 6/1994 | (WO) . |
| 95/15932 | 7/1994 | (WO) . |
| 94/20480 | 9/1994 | (WO) . |
| 94/26731 | 11/1994 | (WO) . |
| 94/27980 | 12/1994 | (WO) . |
| 95/00501 | 1/1995 | (WO) . |
| 95/15316 | 6/1995 | (WO) . |
| WO96/03385 | 2/1996 | (WO) . |
| WO96/03387 | 2/1996 | (WO) . |
| WO96/03388 | 2/1996 | (WO) . |
| WO96/41645 | 12/1996 | (WO) . |

OTHER PUBLICATIONS

W. Beaver, *Am. J. Med.,* 77, 38 (1984).
L. Guth et al, *Proc. Natl. Acad. Sci. USA,* 91, 12308 (1994).
G. Hughes et al, *Dermatology,* 184, 54 (1992).
C. Stewart et al, *Clin. Pharmacol. Ther.,* 47, 540 (1990).
K. Tramposch, *Inflammation,* 17, 531 (1993).
S. Lightman and P. Watson, *Am. J. Ophthalmol.,* 108, 95 (1989).
B. Teicher et al., *Cancer Chemother. Pharmacol.,* 33, 515 (1994).
R. Willkens and E. Segre, *Arthritis Rheum.,* 19, 677 (1976).
P. Seideman et al, *Acta Orthop. Scand.,* 64, 285 (1993).
M. Seifert and C. Engler, *Curr. Med. Res. Opin.,* 7, 38 (1980).
F. Breedveld, *Scan. J. Rheumatol.,* 23 (Supp. 100), 31 (1994).
R. Bartlett et al, *Drugs Exptl. Clin. Res.,* 15, 521 (1989).
J. Shaw and R. Greatorex, *Adv. Prostaglandin, Thromboxane, Leukotriene Res.,* 13, 219 (1985).
V. Fimiani et al, *EOS–Revista di Immunologia and Immunofarmacologia,* 13, 58 (1993).
A. Badger et al, *Immunopharm.,* 4, 149 (1982).
J. Shelby et al, *Transplantation Proc,* 19, 1435 (1987).
D. Latter et al, *J. Surg. Res.,* 43, 246 (1987).
J. Tarayre et al, *Arzneim.–Forsch./Drug Res.,* 40, 1125 (1990).
D. Braun et al, *Proc. Am. Soc. Clin. Oncol.,* 4, 21 Meeting, 223 (1985).
Fung–Leung et al, *Transplantation,* 60, 362 (1995).
Caplus Abstract 1996:225716, Nickerson–Nutter et al, The effects of Leukotriene . . . Mar. 1996.*
Caplus 1996:582169, Zhang Wenyu et al , Tumor necrosis, Jun. 1996.*

* cited by examiner

*Primary Examiner*—Alan L. Rotman
*Assistant Examiner*—Rita Desai
(74) *Attorney, Agent, or Firm*—James M. Warner

(57) ABSTRACT

Treatment with a cyclooxygenase-2 inhibitor and a leukotriene $B_4$ receptor antagonist is described as being useful in reducing recipient rejection of transplanted organs and for treatment of autoimmune diseases.

6 Claims, No Drawings

IMMUNOSUPPRESSIVE EFFECTS OF ADMINISTRATION OF A CYCLOOXYGENASE-2 INHIBITOR AND A LEUKOTRIENE B$^4$ RECEPTOR ANTAGONIST

This is a continuation of application Ser. No. 08/600,580, filed Feb. 13, 1996.

FIELD OF THE INVENTION

This invention is in the field of clinical immunology and relates to compositions having immunosuppressive properties. Of particular interest is a method of reducing recipient acute or chronic rejection of transplanted cells or organs, and for treatment of autoimmune diseases, hypersensitivity reactions of the acute or delayed type, allergic disorders, granulomas, meningitis, and septic shock by administering a cyclooxygenase-2 inhibitor and a leukotriene B$_4$ (LTB$_4$) receptor antagonist.

BACKGROUND OF THE INVENTION

Successful organ transplantation requires effective physiological and pharmacological intervention of the immune system of an organ recipient. Immunologic mechanisms are universal within the human species, but histocompatibility variations between organ donor and recipient may lead to rejection of donor tissue by stimulation of the recipient's immune system, except perhaps, in donor-recipient pairing of the monozygotic type. One approach to intervention of immune response in an organ transplant recipient, especially a recipient targeted for an allogenic graft, is by the use of immunosuppressive drugs. These drugs are used to prolong survival of transplanted organs in recipients in cases involving, for example, transplants of kidney, liver, heart, lung, bone marrow and pancreas.

There are several types of immunosuppressive drugs available for use in reducing organ rejection in transplantation. Such drugs fall within three major classes, namely: antiproliferative agents, antiinflammatory-acting compounds and inhibitors of lymphocyte activation.

Examples of the class of cytotoxic or antiproliferative agents are azathioprine, cyclophosphamide and methotrexate. The compound azathioprine acts by interrupting DNA synthesis through inhibition of purine metabolism. The compound cyclophosphamide is an alkylating agent which interferes with enzyme actions and cell proliferation and interrupts DNA synthesis by binding to cellular DNA, RNA, and proteins. The compound methotrexate is a folic acid antagonist which interferes with nucleotide and protein synthesis. Drugs of the antiproliferative class may be effective immunosuppressives in patients with chronic inflammatory disorders and in organ transplant recipients by limiting cell proliferation. These drugs which abrogate mitosis and cell division have severe cytotoxic side effects on normal cell populations which have a high turn-over rate, such as bone marrow cells and cells of the gastrointestinal (GI) tract lining. Accordingly, such drugs often have severe side effects, particularly, lymphopenia, neutropenia, bone marrow depression, hemorrhagic cystitis, liver damage, increased incidence of malignancy, hair loss, GI tract disturbances, and infertility.

A second class of immunosuppressive drugs for use in transplantation is provided by compounds having antiinflammatory action. Representatives of this drug class are generally known as adrenal corticosteroids and have the advantage of not exerting globally systemic cytotoxic effects. These compounds usually act by preventing or inhibiting inflammatory responses or by reducing cytokine production, or by reducing chemotaxis, or by reducing neutrophil, macrophage or lymphocyte activation, or effector function. Typical examples of adrenal corticosteroids are prednisone and prednisolone which affect carbohydrate and protein metabolism as well as immune functions. Compounds of this class are sometimes used in combination with cytotoxic agents, such as compounds of the antiproliferative class because the corticosteroids are significantly less toxic. But the adrenal corticosteroids lack specificity of effect and can exert a broad range of metabolic, antiinflammatory and immune effects. Typical side effects of this class include increased organ-recipient infections and interference with wound healing, as well as disturbing hemodynamic balance, carbohydrate and bone metabolism and mineral regulation.

A third class of immunosuppressive drugs for use in organ transplantation is provided by compounds which are immunomodulatory and generally prevent or inhibit leukocyte activation. Such compounds usually act by blocking activated T-cell effector functions or proliferation, or by inhibiting cytokine production, or by preventing or inhibiting activation, differentiation or effector functions of platelet, granulocyte, B-cell, or macrophage actions. The cyclosporin family of compounds is the leading example of drugs in this class. Such compounds are polypeptide fungal metabolites which have been found to be very effective in suppressing helper T-cells so as to reduce both cellular and humoral responses to newly-encountered antigens. Cyclosporins alter macrophage and lymphocyte activity by reducing cytokine production or secretion and, in particular, by interfering with activation of antigen-specific CD4 cells, by preventing IL-2 secretion and secretion of many T-cell products, as well as by interfering with expression of receptors for these lymphokines on various cell types. Cyclosporin A, in particular, has been used extensively as an immunosuppressive agent in organ transplantation. Other microbial metabolites include cyclosporins such as cyclosporin B and cyclosporin G, and another microbial product known as FK-506. Cyclosporin A suppresses humoral immunity as well as cell-mediated reactions. Cyclosporin A is indicated for organ rejection in kidney, liver, heart, pancreas, bone-marrow and heart-lung transplants. Cyclosporin A is also useful in the treatment of autoimmune and inflammatory diseases, including rheumatoid arthritis, Crohn's disease, Graves, disease, severe psoriasis, aplastic anemia, multiple-sclerosis, alopecia areata, penphigus and penphigoid, dermatomyositis, polymyositis, Behcet's disease, uveitis, pulmonary sarcocidiosis, biliary cirrhosis, myasthenia gravis and atopic dermatitis.

Cyclosporins possess several significant disadvantages. While cyclosporins have provided significant benefits in organ transplantation, cyclosporins are non-specific immunosuppressives. Desirable immune reactions may be reduced against foreign antigens. Tolerated dosages do not provide complete suppression of rejection response. Thus, immunologic reactions to transplanted tissue are not totally impeded, requiring concomitant treatment with prednisone, methylprednisolone, and/or other immunosuppression agents, including monoclonal antibodies such as anti-CD3 or anti-CD5/CD7. Cyclosporins can produce severe side effects in many organ recipients, and show host-variable effects on the liver, kidney, the CNS and GI tract. Significant among the adverse side effects are damage to the kidney and liver, hyperplasia of gum tissue, refractory hypertension and increased incidence of infections and malignancy.

Thus, the need remains for efficacious and selective immunosuppressive drugs in organ transplantation, especially for grafts between less-than-perfectly matched donor-recipient pairs.

Prostaglandins and leukotrienes are lipid mediators produced in a variety of inflammatory disease states. Both are products of metabolism of arachidonic acid. Cyclooxygenases (COX-1 and COX-2) are the enzymes that catalyze the conversion of arachidonic acid to prostaglandins. 5-Lipoxygenase (5-LO) catalyzes the conversion of arachidonic acid to leukotrienes. Products of both pathways have been described in association with transplant rejection in humans and animal models. Excess production of these mediators may play a role in accelerating loss of the transplant function, particularly in the kidney. However, little research has been directed at determining direct effects of eicosanoids on tissue rejection.

Compounds which selectively inhibit cyclooxygenase-2 have been described. U.S. Pat. No. 5,380,738 describes oxazoles which selectively inhibit cyclooxygenase-2. U.S. Pat. No. 5,344,991 describes cyclopentenes which selectively inhibit cyclooxygenase-2. U.S. Pat. No. 5,393,790 describes spiro compounds which selectively inhibit cyclooxygenase-2. WO documents WO94/15932 describes thiophene and furan derivatives which selectively inhibit cyclooxygenase-2. WO94/27980 -describes oxazoles which selectively inhibit cyclooxygenase-2. WO95/00501 describes compounds which selectively inhibit cyclooxygenase-2. WO94/13635 -describes compounds which selectively inhibit cyclooxygenase-2. WO94/20480 describes compounds which selectively inhibit cyclooxygenase-2. WO94/26731 describes compounds which selectively inhibit cyclooxygenase-2. WO documents WO95/15316 describes pyrazolyl sulfonamide derivatives which selectively inhibit cyclooxygenase-2.

Compounds which affect leukotriene $B_4$ receptors have been described. U.S. Pat. No. 5,384,318 describes substituted sulfonamides for the treatment of asthma. U.S. Pat. No. 5,246,965 describes aryl ethers as leukotriene $B_4$ receptor antagonists.

Combined therapies of NSAIDs and other reagents are known in the art. Combination analgesics have been reported (W. Beaver, *Am. J. Med.*, 77, 38 (1984)) although such combinations do not substantially reduce adverse effects. The combination of NSAIDs and steroids have been described. A combination of indomethacin, steroid and lipopolysaccharide has been reported for the treatment of spinal injury (L. Guth et al., *Proc. Natl. Acad. Sci. USA,* 91, 12308 (1994)). G. Hughes et al. describe combinations of corticosteroids with NSAIDs for the treatment of sunburn (Dermatology, 184, 54 (1992)). C. Stewart et al. (*Clin. Pharmacol. Ther.*, 47, 540 (1990)) describe the combination of naproxen and methotrexate as safe, although concurrent administrations of methotrexate with other NSAIDs have been reported to be toxic and sometimes fatal. A combination of a dual 5-lipoxygenase/cyclooxygenase inhibit-or with a glucocorticoid is described for the treatment of skin disorders (K. Tramposch, *Inflammation,* 17, 531 (1993)). Combinations of NSAIDs and steroids should be used in the treatment of scleritis only if patients are not responsive to any other treatment (S. Lightman and P. Watson, *Am. J. Ophthalmol.,* 108, 95 (1989)). Combinations of cyclooxygenase inhibitors, lipoxygenase inhibitors, collagenase inhibitors and cytotoxic agents have been used in the treatment of non-small-cell lung cancers (B. Teicher et al., *Cancer. Chemother. Pharmacol.,* 33, 515 (1994)). Combinations of naproxen with other NSAIDs have been described in the treatment of arthritis. R. Willikens and E. Segre (Arthritis Rheum., 19, 677 (1976)) describe the combination of aspirin and naproxen as being more effective than aspirin alone for the treatment of rheumatoid arthritis. Naproxen and acetaminophen together were described for treating the pain associated with arthritis (P. Seideman et al., *Acta Orthop. Scand.,* 64, 285 (1993)). However, combinations of naproxen with indomethacin or ibuprofen offer no advantage in the treatment of arthritis (M. Seifert and C. Engler, *Curr. Med. Res. Opin.*, 7, 38 (1980)).

Tenidap has been described as inhibiting cyclooxygenases and cytokine-modifying [F. Breedveld, Scand. J. Rheumatol., 23 (Supp. 100), 31 (1994)]. WO patent Publication 94/02448, published Feb. 3, 1994, describes hydroxamic acid derivatives as dual 5-lipoxygenase and cyclooxygenase inhibitors having immunosuppressant utility. U.S. Pat. No. 4,595,699, to Terada et al., describes phenyl alkanoic acid derivatives as having analgesic, antiinflammatory and immune regulating activity. R. Bartlett et al. describe thiazolo(3,2-b)(1,2,4)triazin-7-ones as antiinflammatory agents with immunomodulating properties [*Drugs Exptl. Clin. Res.*, 15, 521 (1989)]. J. Shaw and R. Greatorex [Adv. *Prostaglandin, Thromboxane, Leukotriene Res.*, 13, 219 (1985)] describe that whereas aspirin and sodium salicylate prolong graft survival, a cyclooxygenase inhibitor reduced the survival period. V. Fimiani, et al. describe some NSAID's that may have activity in the treatment of autoimmune diseases [*EOS-Revista di Immunologia and Immunofarmacologia,* 13, 58 (1993)]. A. Badger et al. describe an indomethacin enhancement of suppressor cell population [*Immunopharm.*, 4, 149 (1982)]. J. Shelby et al. [*Transplantation Proc.,* 19, 1435 (1987)] describe indomethacin as reversing transfusion-induced graft prolongation. D. Latter et al. indicate that indomethacin was effective as an immunomodulator following burns [*J. Surg. Res.*, 43, 246 (1987)]. J. Tarayre et al. describe indomethacin as having an effect in their delayed hypersensitivity models [*Arzneim.-Forsch./Drug Res.*, 40, 1125 (1990)]. D. Braun et al indicate that a prostaglandin synthetase inhibitor may help prevent chemotherapy-induced decline in immune reactivity [*Proc. Am. Soc. Clin. Oncol.,* 4, 21 Meeting, 223 (1985)]. Administration of tepoxalin (dual 5-LO and COX inhibitor) and cyclosporine has been described [Fung-Leung, et al., *Transplantation,* 60, 362 (1995)] in suppression of graft versus host reaction although the effect of tepoxalin did not appear to be related to the inhibition of arachidonic acid metabolism.

There have been no reported combinations of a cyclooxygenase-2 selective inhibitor and a leukotriene $B_4$ receptor antagonist as having a significant prolongation of graft survival.

DESCRIPTION OF THE INVENTION

Reduction in recipient rejection of a transplanted organ, or treatment of an autoimmune or inflammatory disease, or a hypersensitivity reaction of the acute or delayed type, an allergic reaction or asthmatic disorder, or treatment of dermatitis, arthritis, meningitis, granulomas, vasculitis, septic shock or graft vs. host response may be accomplished by a method to prevent or suppress immune responses in a recipient or treatment subject, which method comprises treating the subject with a therapeutically-effective amount of an immunosuppressive combination of a cyclooxygenase-2 inhibitor and a leukotriene $B_4$ receptor antagonist.

In addition, the invention describes a combination comprising a therapeutically-effective amount of a leukotriene B4 receptor antagonist and a cyclooxygenase-2 inhibitor selected from Dupont Dup 697, Taisho NS-398, meloxicam, flosulide and compounds of Formula I

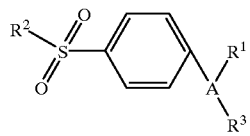

wherein A is a 5- or 6-member ring substituent selected from partially unsaturated or unsaturated heterocyclo and carbocyclic rings;

wherein $R^1$ is at least one substituent selected from heterocyclo, cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

wherein $R^2$ is selected from alkyl, and amino; and wherein $R^3$ is a radical selected from halo, alkyl, alkenyl, alkynyl, oxo, cyano, carboxyl, cyanoalkyl, heterocyclooxy, alkyloxy, alkylthio, alkylcarbonyl, cycloalkyl, aryl, haloalkyl, heterocyclo, cycloalkenyl, aralkyl, heterocycloalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, N-alkyl-N-arylaminosulfonyl; or a pharmaceutically-acceptable salt thereof.

The invention would be useful for, but not limited to, organ transplantation procedures and a variety of disease states. For example, combinations of the invention would be useful to treat a recipient of a graft of a transplanted organ to reduce recipient rejection of the graft or to reduce a donor leukocyte response against the recipient's tissues. Such combinations would be useful, in particular, for transplants of bone marrow, kidney, liver, heart, heart-lung and pancreas organs. Combinations of the invention would also be useful in suppressing immune response in a human or animal subject susceptible to or afflicted with an autoimmune disease or inflammatory disease. Examples of such treatable disease are graft vs. host disease, systemic lupus erythematosis, multiple sclerosis, myasthenia gravis, thyroiditis, Graves' disease, autoimmune hemolytic anemia, aplastic anemia, autoimmune thrombocytopenia purpura, mixed connective tissue disease, idiopathic Addison's disease, Sjogren's syndrome, insulin dependent diabetes mellitus, rheumatoid arthritis, osteoarthritis, skin and muco-epithelial diseases such as psoriasis (in all its forms) lichen, chronic eczema, and pityriasis, glomerulonephritis, inflammatory bowel disease, Crohn's disease, alopecia areata, pemphigus and pemphigoid, dermatomyositis, polymyositis, Behcet's disease, uveitis, pulmonary sarcocidiosis, biliary cirrhosis, and atopic dermatitis. Combinations of the invention would also be useful in suppressing immune response in a human or animal subject susceptible to or afflicted with an allergy, such as an asthmatic condition or reaction, urticaria or with airway hypersensitivity. The invention would also be useful in suppressing immune response in a human or animal subject afflicted with or susceptible to septic shock. Combinations of the invention would also be useful in preventing or suppressing acute or delayed-type hypersensitivity responses or conditions resulting from or associated with hypersensitivity responses such as contact dermatitis, hemolytic anemias, antibody-induced thrombocytopenia, Goodpasture's syndrome, hypersensitivity, pneumonitis, glomerulonephritis, granulomas, thyroiditis, encephelomyelitis, and meningitis. The invention would also be useful in the treatment of cancer, including leukemia, lymphoma and solid tumors, including pancreatic, breast, colon, lung, epithelial and melanoma tumors.

Besides being useful for human treatment, these compounds are also useful for veterinary treatment of mammals, including companion animals and farm animals, such as, but not limited to, horses, dogs, cats, cows, sheep and pigs.

Compositions of the invention would be useful in treating organs prior to transplant. For example, an organ removed from a donor could be stored or transported in a bath containing an immunosuppressive composition of the invention. The immunosuppressive composition would act to inhibit donor leukocyte reactivity.

Compositions of the invention would also be useful in adjunct therapy involving, typically, coadministration with an additional immunosuppressive agent, such as a cyclosporin compound, or Fujisawa FK-506 (macrolide lactone) compound, or rapamycin, or a glucocorticoid, or an antiproliferative agent, or a monoclonal antibody such as an anti-CD3 (anti-T cell receptor antibody) or anti-CD5/CD7 or anti-CD4 agent, or an anti-IL-2 receptor (anti-cytokine receptor antibody) agent or an anti-IL-2 (anti-cytokine antibody), or Nippon NKT-01 (15-deoxyspergualin) or Syntex RS-61443.

The term "cyclooxygenase-2 inhibitor" embraces compounds which selectively inhibit cyclooxygenase-2 over cyclooxygenase-1. Preferably, the compounds have a cyclooxygenase-2 $IC_{50}$ of less than about 0.5 $\mu$M, and also have a selectivity ratio of cyclooxygenase-2 inhibition over cyclooxygenase-1 inhibition of at least 50, and more preferably of at least 100. Even more preferably, the compounds have a cyclooxygenase-1 $IC_{50}$ of greater than about 1 $\mu$M, and more preferably of greater than 20 $\mu$M. Such preferred selectivity may indicate an ability to reduce the incidence of common NSAID-induced side effects.

The term "leukotriene $B_4$ receptor antagonist" embraces compounds which selectively antagonize a leukotriene $B_4$ receptor with an $IC_{50}$ of less than about 10 $\mu$M. More preferably, the leukotriene $B_4$ receptor antagonists have an $IC_{50}$ of less than about 1 $\mu$M.

The phrase "combination therapy" (or "co-therapy"), in defining use of a cyclooxygenase-2 inhibitor agent and a leukotriene B4 receptor antagonist agent, is intended to embrace administration of each agent in a sequential manner in a regimen that will provide beneficial effects of the drug combination. The phrase also is intended to embrace co-administration of these agents in a substantially simultaneous manner, such as in a single capsule having a fixed ratio of these active agents or in multiple, separate capsules for each agent.

The phrase "therapeutically-effective" is intended to qualify the amount of each agent for use in the combination therapy which will achieve the goal of improvement in severity and the frequency of incidence over treatment of each agent by itself, while avoiding adverse side effects typically associated with alternative therapies.

Preferred leukotriene $B_4$ receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products WAY 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and CO. MK-886, Ono ONO-LB-448, Purdue Frederick PF-5901, Rhone-Poulenc Rorer RG 14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SK&F-104493, Leo Denmark SR-2566, Tanabe T-757 and Teijin TEI-1338.

More preferred leukotriene $B_4$ receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Shionogi S-2472, Searle SC-52798, Leo Denmark SR-2566, Tanabe T-757, Sumitamo SM 15178, and American Home Products WAY 121006.

Even more preferred leukotriene $B_4$ receptor antagonists include calcitriol, ontazolast, Bayer Bay-x-1005, Ciba-Geigy CGS-25019C, ebselen, Leo Denmark ETH-615, Lilly LY-293111, Ono ONO-4057, SmithKline Beecham SB-201993, SmithKline Beecham SB-209247, Pfizer 105696, and Terumo TMK-688.

A preferred class of compounds which inhibit cyclooxygenase-2 consists of compounds of Formula I wherein A is selected from oxazolyl, isoxazolyl, thienyl, dihydrofuryl, furyl, pyrrolyl, pyrazolyl, thiazolyl, imidazolyl, isothiazolyl, cyclopentenyl, phenyl, and pyridyl; wherein $R^1$ is selected from 5- and 6-membered heterocyclo, lower cycloalkyl, lower cycloalkenyl and aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is selected from lower alkyl and amino; and wherein $R^3$ is a radical selected from halo, lower alkyl, oxo, cyano, carboxyl, lower cyanoalkyl, heteroaryloxy, lower alkyloxy, lower cycloalkyl, phenyl, lower haloalkyl, 5- or 6-membered heterocyclo, lower hydroxylalkyl, lower aralkyl, acyl, phenylcarbonyl, lower alkoxyalkyl, heteroaryloxy, alkoxycarbonyl, aminocarbonyl, alkylaminocarbonyl, alkylamino, aminoalkyl, alkylaminoalkyl, aryloxy, and aralkoxy; or a pharmaceutically-acceptable salt thereof.

A more preferred class of compounds which inhibit cyclooxygenase-2 consists of compounds of Formula I wherein A is selected from oxazolyl, isoxazolyl, dihydrofuryl, imidazolyl, and pyrazolyl; wherein $R^1$ is selected from 5- and 6-membered heterocyclo, lower cycloalkyl, lower cycloalkenyl and aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is amino; and wherein $R^3$ is a radical selected from oxo, cyano, carboxyl, lower alkoxycarbonyl, lower carboxyalkyl, lower cyanoalkyl, halo, lower alkyl, lower alkyloxy, lower cycloalkyl, phenyl, lower haloalkyl, 5- or 6-membered heterocyclo, lower hydroxylalkyl, lower aralkyl, acyl, phenylcarbonyl, lower alkoxyalkyl, 5- or 6-membered heteroaryloxy, aminocarbonyl, lower alkylaminocarbonyl, lower alkylamino, lower aminoalkyl, lower alkylaminoalkyl, phenyloxy, and lower aralkoxy; or a pharmaceutically-acceptable salt thereof.

An even more preferred class of compounds which inhibit cyclooxygenase-2 consists of compounds of Formula I wherein A is selected from oxazolyl, isoxazolyl, imidazolyl, and pyrazolyl; wherein $R^1$ is phenyl optionally substituted at a substitutable position with one or more radicals selected from methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, cyano, carboxyl, methoxycarbonyl, hydroxyl, hydroxymethyl, trifluoromethoxy, amino, N-methylamino, N,N-dimethylamino, N-ethylamino, N,N-dipropylamino, N-butylamino, N-methyl-N-ethylamino, phenylamino, nitro, methoxymethyl, methylsulfinyl, fluoro, chloro, bromo, methoxy, ethoxy, propoxy, n-butoxy, pentoxy, and methylthio; wherein $R^2$ is amino; and wherein $R^3$ is a radical selected from oxo, cyano, carboxyl, methoxycarbonyl, ethoxycarbonyl, carboxypropyl, carboxymethyl, carboxyethyl, cyanomethyl, fluoro, chloro, bromo, methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, methoxy, ethoxy, propoxy, n-butoxy, pentoxy, cyclohexyl, phenyl, pyridyl, thienyl, thiazolyl, oxazolyl, furyl, pyrazinyl, hydroxylmethyl, hydroxylpropyl, benzyl, formyl, phenylcarbonyl, methoxymethyl, furylmethyloxy, aminocarbonyl, N-methylaminocarbonyl, N,N-dimethylaminocarbonyl, N,N-dimethylamino, N-ethylamino, N,N-dipropylamino, N-butylamino, N-methyl-N-ethylamino, aminomethyl, N,N-dimethylaminomethyl, N-methyl-N-ethylaminomethyl, benzyloxy, and phenyloxy; or a pharmaceutically-acceptable salt thereof.

A family of specific compounds of particular interest within Formula I consists of compounds and pharmaceutically-acceptable salts thereof as follows:

3-(3,4-difluorophenyl)-4-(4-methylsulfonylphenyl)-2-(5H)-furanone;

3-phenyl-4-4-methylsulfonylphenyl)-2-(5H)-furanone;

4-[5-(4-chlorophenyl)-3-(trifluoromethyl)-1H-pyrazol-1-yl]benzenesulfonamide;

4-[5-(4-methylphenyl)-3-(trifluoromethyl)-1H-pyrazol-1-yl]benzenesulfonamide;

4-[5-(3-fluoro-4-methoxyphenyl)-3-(difluoromethyl)-1H-pyrazol-1-yl]benzenesulfonamide;

3-[1-[4-(methylsulfonyl)phenyl]-4-trifluoromethyl-1H-imidazol-2-yl]pyridine;

2-methyl-5-[1-[4-(methylsulfonyl)phenyl]-4-trifluoromethyl-1H-imidazol-2-yl]pyridine;

4-[2-(5-methylpyridin-3-yl)-4-(trifluoromethyl)-1H-imidazol-1-yl]benzenesulfonamide;

4-[5-methyl-3-phenylisoxazol-4-yl]benzenesulfonamide;

4-[5-hydroxyethyl-3-phenylisoxazol-4-yl]benzenesulfonamide;

[2-trifluoromethyl-5-(3,4-difluorophenyl)-4-oxazolyl]benzenesulfonamide;

4-[2-methyl-4-phenyl-5-oxazolyl]benzenesulfonamide; and

4-[5-(3-fluoro-4-methoxyphenyl-2-trifluoromethyl)-4-oxazolyl]benzenesulfonamide.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about six carbon atoms. Examples of alkenyl radicals include ethenyl, propenyl, allyl, propenyl, butenyl and 4-methylbutenyl. The term "alkynyl" denotes linear or branched radicals having at least one carbon-carbon triple bond and having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. Examples of such radicals include propargyl, butynyl, and the like. The terms "alkenyl" and "lower alkenyl", embrace radicals having "cis" and "trans" orientations, or alternatively, "E" and "Z" orientations. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "cycloalkenyl" embraces partially unsaturated carbocyclic radicals having three to twelve carbon atoms. More preferred cycloalkenyl radicals are "lower cycloalkenyl" radicals having four to about eight carbon atoms. Examples of such radicals include cyclobutenyl, cyclopentenyl and cyclohexenyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having one to six carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide haloalkoxy radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Aryl moieties may also be substituted at a substitutable position with one or more substituents selected independently from alkyl, alkoxyalkyl, alkylaminoalkyl, carboxyalkyl, alkoxycarbonylalkyl, aminocarbonylalkyl, alkoxy, aralkoxy, hydroxyl, amino, halo, nitro, alkylamino, acyl, cyano, carboxy, aminocarbonyl, alkoxycarbonyl and aralkoxycarbonyl. The term "heterocyclo" embraces saturated, partially unsaturated and unsaturated heteroatom-containing ring-shaped radicals, where the heteroatoms may be selected from nitrogen, sulfur and oxygen. Examples of saturated heterocyclo radicals include saturated 3 to 6-membered heteromonocylic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclo radicals include dihydrothiophene, dihydropyran, dihydrofuran and dihydrothiazole. The term "heteroaryl" embraces unsaturated heterocyclo radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclo group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclo group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclo group containing 1 to 2 sulfur atoms and 1 to 3 nitrogen atoms (e.g., benzothiazolyl, benzothiadiazolyl, etc.) and the like. The term "heteroaryl" also embraces radicals where heterocyclo radicals are fused with aryl radicals. Examples of such fused bicyclic radicals include benzofuran, benzothiophene, and the like. Said "heterocyclo group" may have 1 to 3 substituents such as alkyl, hydroxyl, halo, alkoxy, oxo, amino and alkylamino. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyll" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include methylthiomethyl. The term "alkylsulfinyl" embraces radicals containing a linear or branched alkyl radical, of one to about ten carbon atoms, attached to a divalent —S(=O)— radical. More preferred alkylsulfinyl radicals are "lower alkylsulfinyll" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as "alkylsulfonyl", denotes a divalent radical, —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denote NH$_2$O$_2$S—. The term "acyl" denotes a radical provided by the residue after removal of hydroxyl from an organic acid. Examples of such acyl radicals include alkanoyl and aroyl radicals. Examples of such lower alkanoyl radicals include formyl, acetyl, propionyl, butyryl, isobutyryl, valeryl, isovaleryl, pivaloyl, hexanoyl, trifluoroacetyl. The term "carbonyl", whether used alone or with other terms, such as "alkoxycarbonyl", denotes —(C=O)—. The term "aroyl" embraces aryl radicals with a carbonyl radical as defined above. Examples of aroyl include benzoyl, naphthoyl, and the like and the aryl in said aroyl may be additionally substituted. The terms "carboxy" or "carboxyl", whether used alone or with other terms, such as "carboxyalkyl", denotes —CO$_2$H. The term "carboxyalkyl" embraces alkyl radicals substituted with a carboxy radical. More preferred are "lower carboxyalkyl" which embrace lower alkyl radicals as defined above, and may be additionally substituted on the alkyl radical with halo. Examples of such lower carboxyalkyl radicals include carboxymethyl, carboxyethyl and carboxypropyl. The term "alkoxycarbonyl" means a radical containing an alkoxy radical, as defined above, attached via an oxygen atom to a carbonyl-radical. More preferred are "lower alkoxycarbonyl" radicals with alkyl porions having one to six carbons. Examples of such lower alkoxycarbonyl (ester) radicals include substituted or unsubstituted methoxycarbonyl, ethoxycarbonyl, propoxycarbonyl, butoxycarbonyl and hexyloxycarbonyl. The terms "alkylcarbonyl", "arylcarbonyl" and "aralkylcarbonyl" include radicals having alkyl, aryl and aralkyl radicals, as defined herein, attached to a carbonyl radical. Examples of such radicals include substituted or unsubstituted methylcarbonyl, ethylcarbonyl, phenylcarbonyl and benzylcarbonyl. The term "aralkyl" embraces aryl-substituted alkyl radicals such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy. The terms benzyl and phenylmethyl are interchangeable. The term "heterocycloalkyl" embraces saturated and partially unsaturated heterocyclo-substituted alkyl radicals, such as pyrrolidinylmethyl, and heteroaryl-substituted alkyl radicals, such as pyridylmethyl, quinolylmethyl, thienylmethyl, furylethyl, and quinolylethyl. The heteroaryl in said heteroaralkyl may be additionally substituted with halo, alkyl, alkoxy, halkoalkyl and haloalkoxy. The term "aralkoxy" embraces aralkyl radicals attached through an oxygen atom to other radicals. The term "aralkoxyalkyl" embraces aralkoxy radicals attached through an oxygen atom to an alkyl radical. The term "aralkylthio" embraces aralkyl radicals attached to a sulfur atom. The term "aralkylthioalkyl" embraces aralkylthio radicals attached through a sulfur atom to an alkyl radical. The term "aminoalkyl" embraces alkyl radicals substituted with amino radicals. More preferred are "lower aminoalkyl" radicals. Examples of such radicals include aminomethyl, aminoethyl, and the like. The term "alkylamino" denotes amino groups which are substituted with one or two alkyl radicals. Preferred are "lower alkylamino" radicals having alkyl porions having one to six carbon atoms. Suitable lower alkylamino may be monosubstituted N-alkylamino or disubstituted N,N-alkylamino, such as N-methylamino, N-ethylamino, N,N-dimethylamino, N,N-diethylamino or the like. The term "arylamino" denotes amino groups which are substituted with one or two aryl radicals, such as N-phenylamino. The "arylamino" radicals may be further substituted on the aryl ring portion of the radical. The term "aralkylamino" embraces amino groups which are substituted with one or two aralkyl radicals. The terms "N-arylaminoalkyl" and "N-aryl-N-alkyl-aminoalkyl" denote aminoalkyl groups which are substituted with one aryl radical or one aryl and one alkyl radical, respectively. Examples of such radicals include N-phenylaminomethyl and N-phenyl-N-methylaminomethyl. The term "aminocarbonyl" denotes an amide group of the formula —C(=O)NH$_2$. The term "alkylaminocarbonyl" denotes an aminocarbonyl group which has been substituted with one or two alkyl radicals on the amino nitrogen atom. Preferred are "N-alkylaminocarbonyl" and "N,N-dialkylaminocarbonyl" radicals. More preferred are "lower N-alkylaminocarbonyl"

and "lower N,N-dialkylaminocarbonyl" radicals with lower alkyl portions as defined above. The term "alkylaminoalkyl" embraces radicals having one or more alkyl radicals attached to an aminoalkyl radical. The term "aryloxyalkyl" embraces radicals having an aryl radicals attached to an alkyl radical through a divalent oxygen atom. The term "arylthioalkyl" embraces radicals having an aryl radicals attached to an alkyl radical through a divalent sulfur atom.

The present invention comprises a pharmaceutical composition comprising a therapeutically-effective amount of a leukotriene $B_4$ receptor antagonist and a cyclooxygenase-2 inhibitor compound in association with at least one pharmaceutically-acceptable carrier, adjuvant or diluent.

The present invention also comprises a method of treating immune-associated disorders in a subject, the method comprising treating the subject having or susceptible to such disorder with a therapeutically-effective amount of a leukotriene B4 receptor antagonist and a cyclooxygenase-2 inhibitor compound. The method of the present invention also includes prophylactic treatment.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclo, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicylic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The cyclooxygenase-2 inhibitor compounds of the invention can be synthesized according to the following procedures of Schemes I–X, wherein the $R^1$–$R^3$ substituents are as defined for Formula I, above, except where further noted.

Scheme I

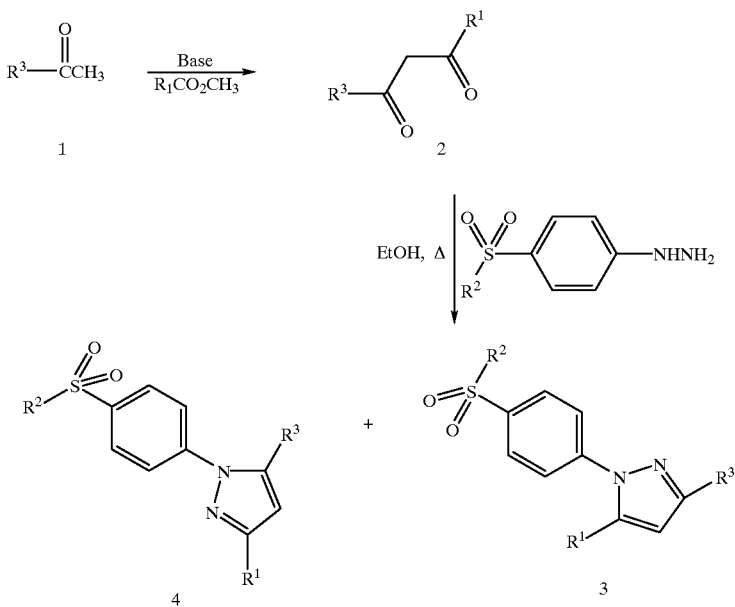

Synthetic Scheme I shows the preparation of cyclooxygenase-2 inhibitor compounds, as described in U.S. patent application Ser. No. 08/223,629, which is incorporated by reference, embraced by Formula I. In step 1, ketone 1 is treated with a base, preferably NaOMe or NaH, and an ester, or ester equivalent, to form the intermediate diketone 2 (in the enol form) which is used without further purification. In step 2, diketone 2 in an anhydrous protic solvent, such as absolute ethanol or acetic acid, is treated with the hydrochloride salt or the free base of a substituted hydrazine at reflux to afford a mixture of pyrazoles 3 and 4. Recrystallization or chromatography affords 3 usually as a solid. Similar pyrazoles can be prepared by methods described in U.S. Pat. Nos. 4,146,721, 5,051,518, 5,134,142 and 4,914,121 which also are incorporated by reference.

Scheme II

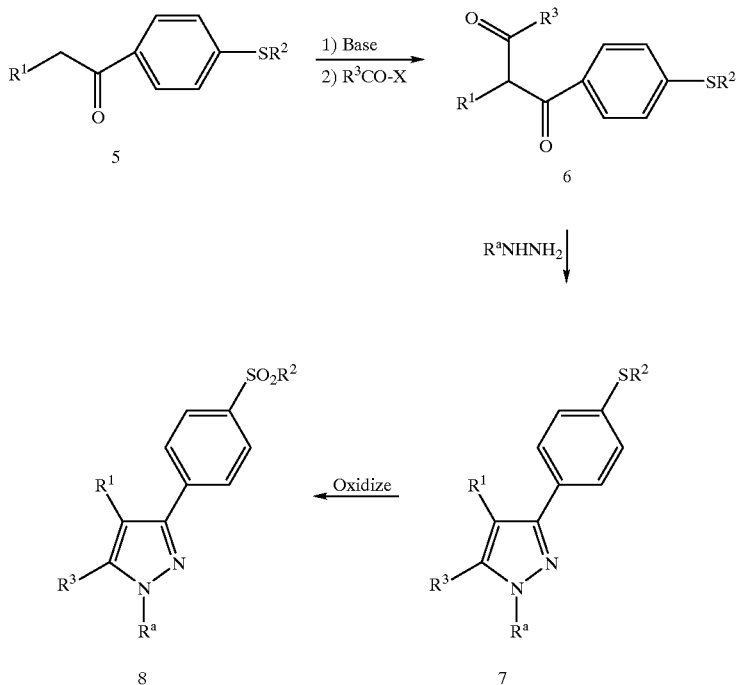

Scheme II shows the four step procedure for forming cyclooxygenase-2 inhibitor pyrazoles 8 as described in U.S. patent application Ser. No. 08/278,297 (where $R^a$ is hydrido or alkyl) from ketones 5. In step 1, ketone 5 is reacted with a base, such as lithium bis(trimethylsilyl)amide or lithium diisopropylamide (LDA) to form the anion. In step 2, the anion is reacted with an acetylating reagent to provide diketone 6. In step 3, the reaction of diketone 6 with a hydrazine or a substituted hydrazine, gives pyrazole 7. In step 4, the pyrazole 7 is oxidized with an oxidizing reagent, such as Oxone® (potassium peroxymonosulfate), 3-chloroperbenzoic acid (MCPBA) or hydrogen peroxide, to give a mixture of the desired 3-(alkylsulfonyl)phenyl-pyrazole 8 and the 5-(alkylsulfonyl)phenyl-pyrazole isomer. The desired pyrazole 8, usually a white or pale yellow solid, is obtained in pure form either by chromatography or recrystallization.

Alternatively, diketone 6 can be formed from ketone 5 by treatment with a base, such as sodium hydride, in a solvent, such as dimethylformamide, and further reacting with a nitrile to form an aminoketone. Treatment of the aminoketone with acid forms the diketone 6. Similar pyrazoles can be prepared by methods described in U.S. Pat. No. 3,984,431 which is incorporated by reference.

Scheme III

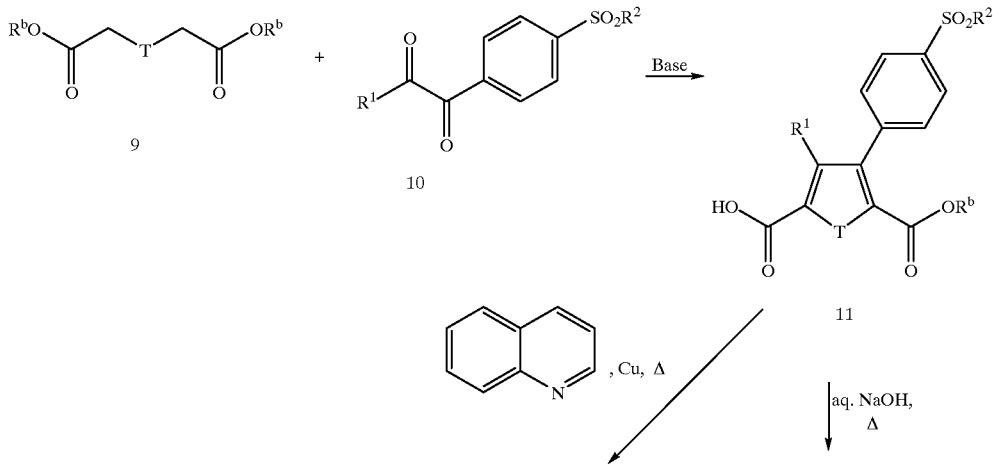

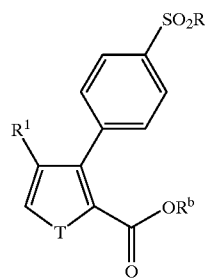
12
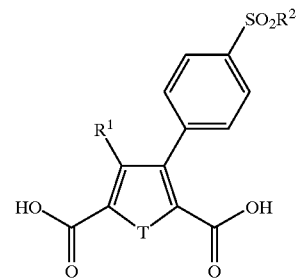
13
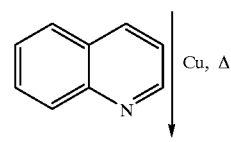
Cu, Δ
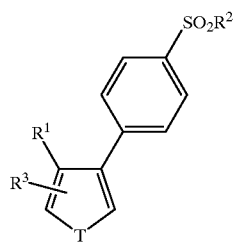
15
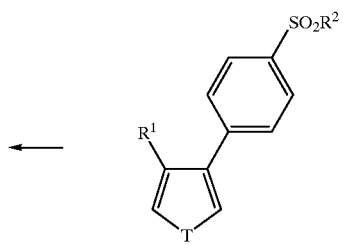
14
Cyclooxygenase-2 inhibitor diaryl/heteroaryl thiophenes (where T is S, and $R^b$ is alkyl) can be prepared by the methods described in U.S. Pat. Nos. 4,427,693, 4,302,461, 4,381,311, 4,590,205, and 4,820,827, and PCT documents WO 95/00501 and WO94/15932, which are incorporated by reference. Similar pyrroles (where T is N), furanones and furans (where T is O) can be prepared by methods described in PCT documents WO 95/00501 and WO94/15932.
Scheme IV
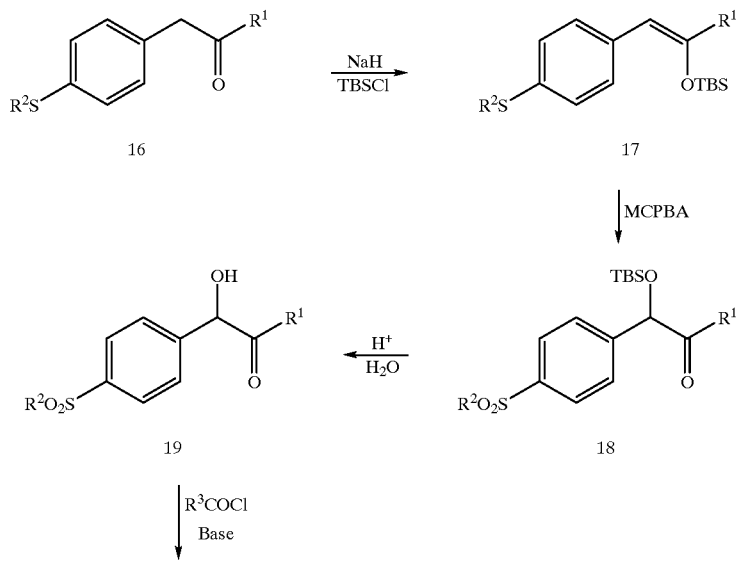

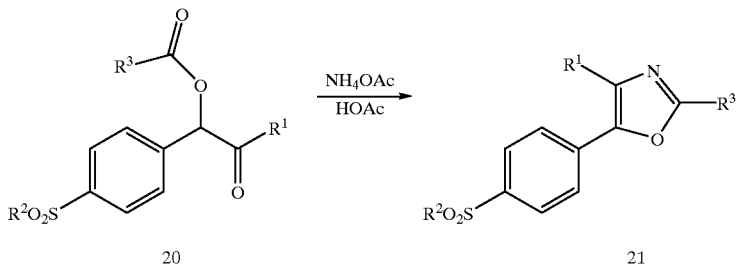

Cyclooxygenase-2 inhibitor diaryl/heteroaryl oxazoles can be prepared by the methods described in U.S. Pat. Nos. 3,743,656, 3,644,499 and 3,647,858, and PCT documents WO 95/00501 and WO94/27980, which are incorporated by reference.

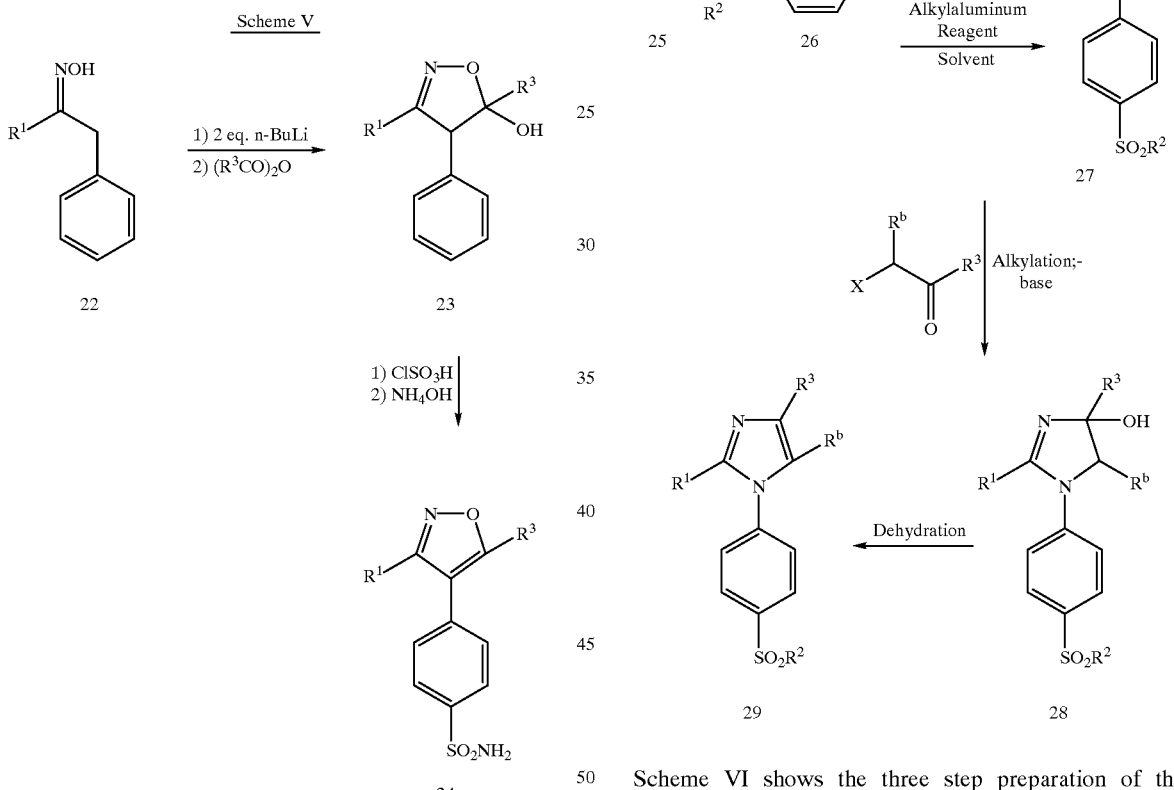

Cyclooxygenase-2 inhibitor diaryl/heteroaryl isoxazoles can be prepared by the methods described in U.S. application Ser. No. 08/387,680, PCT documents WO92/05162, and WO92/19604, and European Publication EP 26928 which are incorporated by reference. Sulfonamides 24 can be formed from the hydrated isoxazole 23 in a two step procedure. First, hydrated isoxazole 23 is treated at about 0° C. with two or three equivalents of chlorosulfonic acid to form the corresponding sulfonyl chloride. In step two, the sulfonyl chloride thus formed is treated with concentrated ammonia to provide the sulfonamide derivative 24.

Scheme VI shows the three step preparation of the cyclooxygenase-2 inhibitor imidazoles 29 of the present invention. In step 1, the reaction of substituted nitrites ($R^1CN$) 25 with primary phenylamines 26 in the presence of alkylaluminum reagents such as trimethylaluminum, triethylaluminum, dimethylaluminum chloride, diethylaluminum chloride in the presence of inert solvents such as toluene, benzene, and xylene, gives amidines 27. In step 2, the reaction of amidine 27 with 2-haloketones (where X is Br or Cl) in the presence of bases, such as sodium bicarbonate, potassium carbonate, sodium carbonate, potassium bicarbonate or hindered tertiary amines such as N,N'-diisopropylethylamine, gives the 4,5-dihydroimidazoles 28 (where $R^b$ is alkyl). Some of the suitable solvents for this reaction are isopropanol, acetone and dimethylformamide. The reaction may be carried out at temperatures of about 20° C. to about 90° C. In step 3, the 4,5-dihydroimidazoles 28 may be dehydrated in the presence of an acid catalyst such as 4-toluenesulfonic acid or mineral acids to form the 1,2-disubstituted imidazoles 29 of the invention. Suitable solvents for this dehydration step are e.g., toluene, xylene and benzene. Trifluoroacetic acid can be used as solvent and catalyst for this dehydration step.

In some cases (e.g., where $R^3$=methyl or phenyl) the intermediate 28 may not be readily isolable. The reaction, under the conditions described above, proceeds to give the targeted imidazoles directly.

Similarly, imidazoles can be prepared having the sulfonylphenyl moiety attached at position 2 and $R^1$ attached at the nitrogen atom at position 1. Diaryl/heteroaryl imidazoles can be prepared by the methods described in U.S. Pat. No. 4,822,805, U.S. application Ser. No. 08/282,395 and PCT document WO 93/14082, which are incorporated by reference.

The subject imidazole cyclooxygenase-2 inhibitor compounds 36 of this invention may be synthesized according to the sequence outlined in Scheme VII. Aldehyde 30 may be converted to the protected cyanohydrin 31 by reaction with a trialkylsilyl cyanide, such as trimethylsilyl cyanide (TMSCN) in the presence of a catalyst such as zinc iodide ($ZnI_2$) or potassium cyanide (KCN). Reaction of cyanohydrin 31 with a strong base followed by treatment with benzaldehyde 32 (where $R^2$ is alkyl) and using both acid and base treatments, in that order, on workup gives benzoin 33. Examples of strong bases suitable for this reaction are lithium diisopropylamide (LDA) and lithium hexamethyldisilazane. Benzoin 33 may be converted to benzil 34 by reaction with a suitable oxidizing agent, such as bismuth oxide or manganese dioxide, or by a Swern oxidation using dimethyl sulfoxide (DMSO) and trifluoroacetic anhydride.

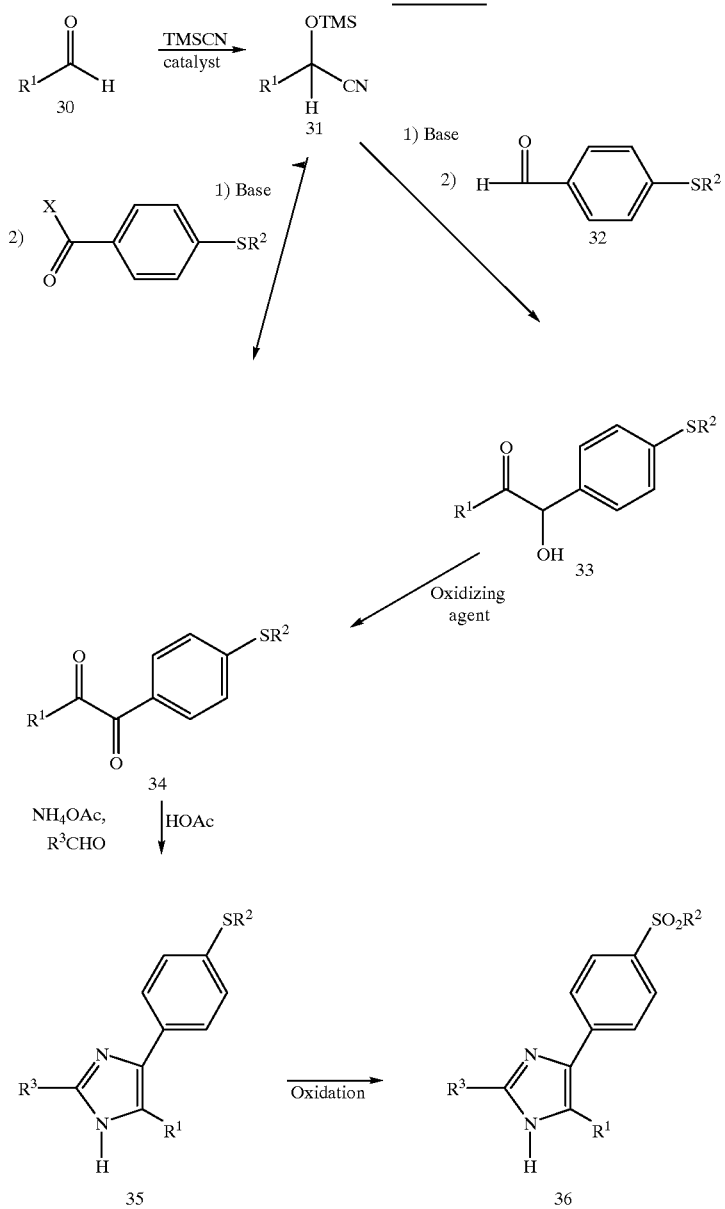

Scheme VII

Benzil 34 may be obtained directly by reaction of the anion of cyanohydrin 31 with a substituted benzoic acid halide. Any of compounds 33 and 34 may be used as intermediates for conversion to imidazoles 35 (where $R^2$ is alkyl) according to chemical procedures known by those skilled in the art and described by M. R. Grimmett, "*Advances in Imidazole Chemistry*" in Advances in Heterocyclic Chemistry, 12, 104 (1970). The conversion of 34 to imidazoles 35 is carried out by reaction with ammonium acetate and an appropriate aldehyde ($R^3$CHO) in acetic acid. Benzoin 36 may be converted to imidazoles 38 by reaction with formamide. In addition, benzoin 36 may be converted to imidazoles by first acylating with an appropriate acyl group ($R^3$CO—) and then treating with ammonium hydroxide. Those skilled in the art will recognize that the oxidation of the sulfide (where $R^2$ is methyl) to the sulfone may be carried out at any point along the way beginning with compounds 35, and including oxidation of imidazoles 38, using, for examples, reagents such as hydrogen peroxide in acetic acid, m-chloroperoxybenzoic acid (MCPBA) and potassium peroxymonosulfate (OXONE®).

Diaryl/heteroaryl imidazoles can be prepared by the methods described in U.S. Pat. Nos. 3,707,475, 4,686,231, 4,503,065, 4,472,422, 4,372,964, 4,576,958, 3,901,908, U.S. application Ser. No. 08/281,903 European publication EP 372,445, and PCT document WO 95/00501, which are incorporated by reference.

Scheme VIII

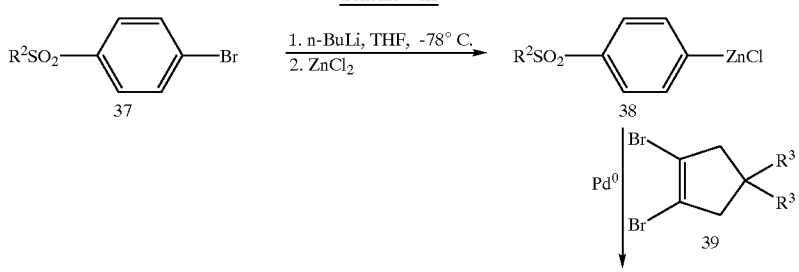

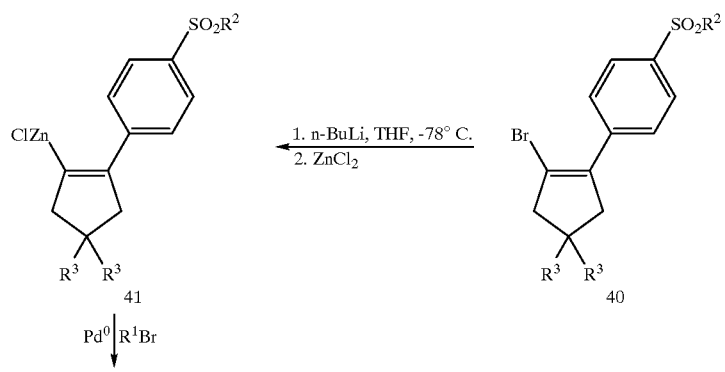

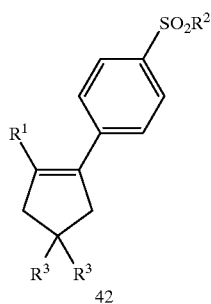

Diaryl/heteroaryl cyclopentene cyclooxygenase-2 inhibitors can be prepared by the methods described in U.S. Pat. No. 5,344,991, and PCT document WO 95/00501, which are incorporated by reference.

Scheme IX

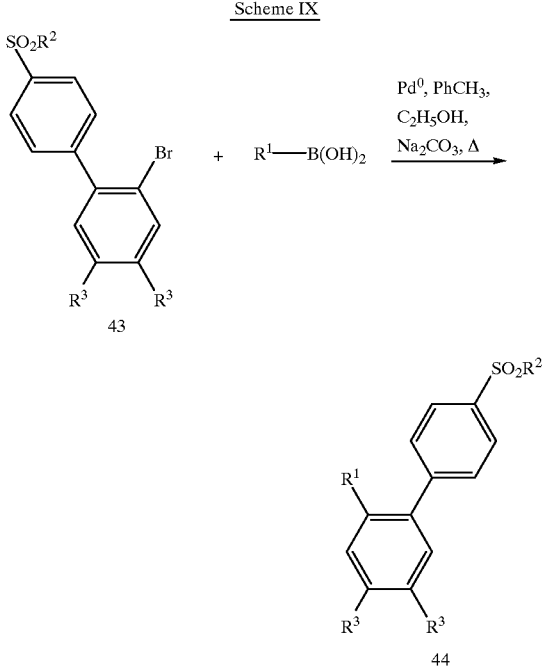

Similarly, Synthetic Scheme IX shows the procedure for the preparation of 1,2-diarylbenzene cyclooxygenase-2 inhibitor agents 44 from 2-bromo-biphenyl intermediates 43 (prepared similar to that described in Synthetic Scheme VIII) and the appropriate substituted phenylboronic acids. Using a coupling procedure similar to the one developed by Suzuki et al. [*Synth. Commun.*, 11, 513 (1981)], intermediates 43 are reacted with the boronic acids in toluene/ethanol at reflux in the presence of a Pd° catalyst, e.g., tetrakis (triphenylphosphine)palladium(0), and 2M sodium carbonate to give the corresponding 1,2-diarylbenzene antiinflammatory agents 44 of this invention. Such terphenyl compounds can be prepared by the methods described in U.S. application Ser. No. 08/346,433, which is incorporated by reference.

Scheme X

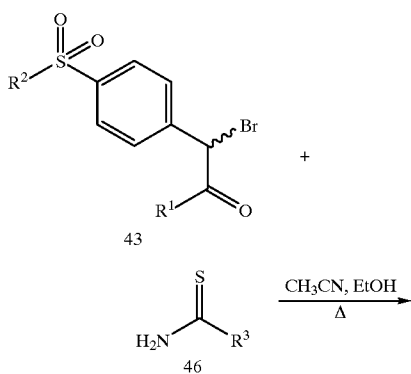

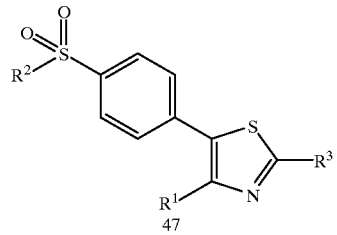

Diaryl/heteroaryl thiazole cyclooxygenase-2 inhibitors can be prepared by the methods described in U.S. Pat. Nos. 4,051,250, 4,632,930, U.S. application Ser. No. 08/281,288, European Application EP 592,664, and PCT document WO 95/00501, which are incorporated by reference. Isothiazoles can be prepared as described in PCT document WO 95/00501.

Diaryl/heteroaryl pyridine cyclooxygenase-2 inhibitors can be prepared by the methods described in U.S. Pat. Nos. 5,169,857, 4,011,328, 4,533,666, U.S. application Ser. No. 08/386,843 and U.S. application Ser. No. 08/387,150 which are incorporated by reference.

The following examples contain detailed descriptions of the methods of preparation of combinations with compounds of Formula I. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

EXAMPLE 1

4-[5-(4-Chlorophenyl)-3-(trifluoromethyl)-1H-pyrazol-1-yl]benzenesulfonamide

Step 1: Preparation of 4,4,4-trifluoro-1-[4-(chloro)phenyl]-butane-1,3-dione.

Ethyl trifluoroacetate (23.52 g, 166 mmol) was dissolved in methyl tert-butyl ether (75 mL). To the stirred solution was added 25 weight % sodium methoxide (40 mL, 177 mmol). 4'-Chloroacetophenone (23.21 g, 150 mmol) was dissolved in methyl tert-butyl ether (20 mL) and added to the reaction dropwise. After stirring overnight (15.75 hours), 3N HCl (70 mL) was added. The organic layer was collected, washed with brine (75 mL), dried over MgSO$_4$, filtered, and concentrated in vacuo to give a yellow-orange solid. The solid was recrystallized from isooctane to give the dione (31.96 g, 85%): mp 66–67° C.

Step 2: Preparation of 4-[5-(4-chlorophenyl)-3-(trifluoromethyl)-1H-pyrazol-1-yl]benzenesulfonamide.

4-Sulphonamidophenyl hydrazine hydrochloride (982 mg, 4.4 mmol, 1.1 equiv.) was added to a stirred solution of 4,4,4-trifluoro-1-[4-(chloro)phenyl]-butane-1,3-dione from Step 1 (1.00 g, 4.0 mmol) in ethanol (50 mL). The reaction was heated to reflux and stirred for 20 hours. After cooling to room temperature, the reaction mixture was concentrated in vacuo. The residue was taken up in ethyl acetate and washed with water and brine. The residue was dried over MgSO$_4$, filtered, and concentrated in vacuo to give a light brown solid. The solid was recrystallized from ethyl acetate and isooctane to give the pyrazole (1.28 g, 80%): mp 143–145° C.; EI GC-MS M+=401.

EXAMPLE 2

4-[5-(3-Fluoro-4-methoxyphenyl)-3-(difluoromethyl)-1H-pyrazol-1-yl]benzenesulfonamide Step 1: Preparation of 3'-fluoro-4'-methoxy-acetophenone.

Acetyl chloride (51.0 g, 0.65 mol) was added dropwise to a stirred solution of aluminum chloride (80.0 g, 0.6 mol) and chloroform (750 mL), maintaining the temperature between 5–10° C. The mixture was stirred for 10 minutes at 5° C. before the dropwise addition of 2-fluoroanisole (62.6 g, 0.5 mol). The mixture was stirred at 0–10° C. for 1 hour and poured into ice (1 L). The resultant layers were separated and the aqueous layer was extracted with dichloromethane (2×250 mL). The combined organic layers were washed with water (2×150 mL), dried over anhydrous MgSO$_4$, filtered and concentrated in vacuo to a volume of 300 mL. Hexanes were added and a white solid formed which was isolated by filtration and air dried. This material was recrystallized from a mixture of dichloromethane and hexanes to afford material suitable for use in the next step (77.2 g, 92%): mp 92–94° C.

Step 2: Preparation of 4,4-difluoro-1-(3-fluoro-4-methoxyphenyl)-butane-1,3-dione.

Ethyl difluoroacetate (4.06 g, 32.7 mmol) was dissolved in methyl tert-butyl ether (50 mL). To the stirred solution was added 25 weight % sodium methoxide (7.07 g, 32.7 mmol) followed by 3'-fluoro-4'-methoxyacetophenone from Step 1 (5.0 g, 29.7 mmol). After stirring for 16 hours, 1N HCl (50 mL) was added. The organic layer was collected and washed with water (2×50 mL), dried over anhydrous MgSO$_4$, filtered, and added to hexanes to precipitate a tan solid (7.0 g, 96%): mp 70–72° C.

Step 3: Preparation of 4-[5-(3-fluoro-4-methoxyphenyl)-3-(difluoromethyl)-1H-pyrazol-1-yl]benzenesulfonamide.

4,4-Difluoro-1-(3-fluoro-4-methoxyphenyl)-butane-1,3-dione from Step 2 (7.0 g, 28.4 mmol) was dissolved in ethanol (150 mL). To the stirred mixture was added 4-sulphonamidophenyl hydrazine hydrochloride (7.4 g, 33 mmol) and stirred at reflux overnight (16 hours). The mixture was cooled and water was added until crystals slowly appeared. The product was isolated by filtration and air dried to provide the desired product as a light tan solid (9.8 g, 87%): mp 159–161° C. Anal. Calc'd. for C$_{17}$H$_{14}$N$_3$SO$_3$F$_3$: C, 51.38; H, 3.55; N, 10.57. Found: C, 51.46; H, 3.52; N, 10.63.

EXAMPLE 3

7-[3-[2-(Cyclopropylmethyl)-3-methoxy-4-[(methylamino)carbonyl]phenoxy]propoxy]-3,4-dihydro-8-propyl-2H-1-benzopyran-2-propanoic acid is prepared as in U.S. Pat. No. 5,310,951, which is incorporated by reference.

BIOLOGICAL EVALUATION

A combination of a cyclooxygenase-2 inhibitor and a leukotriene B$_4$ receptor antagonist is evaluated as described in the following tests.

Transplantation and Evaluation of Graft Rejection

The method of skin grafting used has been previously described [D. Steinmuller, Skin Grafting. Surgical Techniques in Immunology, Methods Enzymol. 108, 20 (1984)]. Briefly, a tailskin from an 8–12 week old male B10.Br mouse is removed and stored in cold saline. Male C57BL/10 mice are anesthetized, and their backs are shaved. The backs are scrubbed with alcohol, and a 1 cm$^2$ piece of skin is removed. A similar size piece of skin is cut from the tailskin of the B10.Br mouse and placed in the excised area on the C57BL/10 animal's back. A petroleum jelly coated bandage is placed over the graft and held in place by a bandage. Compounds are prepared as a suspension in 0.5% methylcellulose (Sigma, St. Louis, Mo.), and 0.025% Tween® 20 (Sigma). The compounds are administered by i.p. injection in a volume of 0.1 ml beginning on the day of skin grafting and continuing until transplant rejection. Cyclosporin A (csa) is purchased as "Sandimmune Injection" at a pharmacy. Compounds are administered alone or as combinations of a COX-2 and a leukotriene B$_4$ receptor antagonist. Bandages are left in place until 8 days post grafting. At that time they are removed, and the grafts are observed daily for signs of rejection. Rejection is determined by complete blackening or scabbing of the grafted skin. The animals are dosed at one of the following dosing ranges:

Example 1@M, W, F @ 10 mpk/day;
Example 2@30 mpk/day, q.d.;
Example 3@10 mpk/day, q.d.;
csa@5 mpk/day, b.d.

The combinations of a COX-2 inhibitor or the leukotriene B$_4$ receptor antagonist should be active in delaying graft rejection at a dosage of about 10–20 mg per kg body weight. The coadministration of a COX-2 inhibitor or the leukotriene B$_4$ receptor antagonist with a low dose of the immunosuppressant Cyclosporin A should enhance prolongation of graft survival and may have additive or synergistic effects when combined with cyclosporin.

EXAMPLE 4

A formulation is prepared having the following components:

700 mg of a cyclooxygenase-2 inhibitor and 700 mg of a leukotriene B$_4$ receptor antagonist.

EXAMPLE 5

A formulation is prepared having the following components:

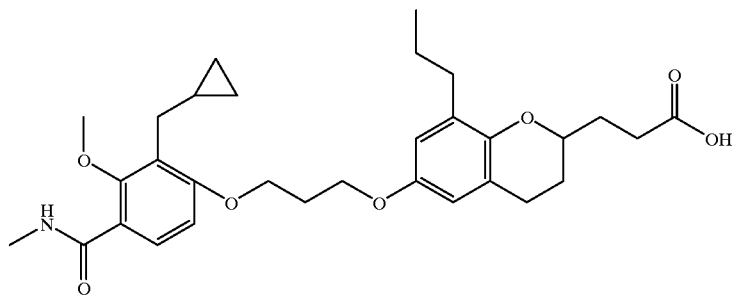

350 mg of 4-[5-(3-fluoro-4-methoxyphenyl)-3-(difluoromethyl)-1H-pyrazol-1-yl]benzenesulfonamide and 700 mg of 7-[3-[2-(cyclopropylmethyl)-3-methoxy-4-[(methylamino)carbonyl]phenoxy]propoxy]-3,4-dihydro-8-propyl-2H-1-benzopyran-2-propanoic acid.

Also embraced within this invention is a class of pharmaceutical compositions comprising the active compounds of this combination therapy in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds that are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferably in the range of about 0.5 to 500 mg and most preferably between about 1 and 100 mg. A daily dose of about 0.01 to 100 mg/kg body weight, preferably between about 0.05 and about 20 mg/kg body weight and most preferably between about 0.1 to 10 mg/kg body weight, may be appropriate. The daily dose can be administered in one to four doses per day.

In the case of psoriasis and other skin conditions, it may be preferable to apply a topical preparation of compounds of this invention to the affected area two to four times a day.

For disorders of the eye or other external tissues, e.g., mouth and skin, the formulations are preferably applied as a topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium laurylsulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or-liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxy-propylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A method to suppress immune response in a subject susceptible to or afflicted with rejection of an organ transplanted to said subject, said method comprising treating the subject with a therapeutically-effective amount of a leukotriene $B_4$ receptor antagonist and a cyclooxygenase-2 inhibitor selected from compounds of

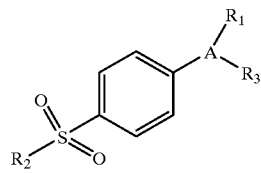

I wherein A is pyrazolyl;
wherein $R^1$ is at least one substituent selected from cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;
wherein $R^2$ is amino; and
wherein $R^3$ is a radical selected from halo, alkyl, alkenyl, alkynyl, oxo, cyano, carboxyl, cyanoalkyl, heterocyclooxy, alkyloxy, alkylthio, alkylcarbonyl, cycloalkyl, aryl, haloalkyl, cycloalkenyl, aralkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, and N-alkyl-N-arylaminosulfonyl;
or a pharmaceutically-acceptable salt thereof.

2. The method of claim 1 wherein said leukotriene $B_4$ receptor antagonist and said cycloxygenase-2 inhibitor are administered in a sequential manner.

3. The method of claim 1 wherein said leukotriene $B_4$ receptor antagonist and said cycloxygenase-2 inhibitor are administered in a substantially simultaneous manner.

4. The method of claim 1 wherein A is pyrazolyl; wherein $R^1$ is selected from aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is amino; and wherein $R^3$ is a radical selected from oxo, cyano, carboxyl, lower alkoxycarbonyl, lower carboxyalkyl, lower cyanoalkyl, halo, lower alkyl, lower alkyloxy, lower cycloalkyl, phenyl, lower haloalkyl, lower hydroxylalkyl, lower aralkyl, acyl, phenylcarbonyl, lower alkoxyalkyl, aminocarbonyl, lower alkylaminocarbonyl, lower alkylamino, lower aminoalkyl, lower alkylaminoalkyl, phenyloxy, and lower aralkoxy; or a pharmaceutically-acceptable salt thereof.

5. The method of claim 4 wherein A is pyrazolyl; wherein $R^1$ is phenyl optionally substituted at a substitutable position with one or more radicals selected from methyl, ethyl, isopropyl, butyl, tertbutyl, isobutyl, pentyl, hexyl, trifluoromethyl, cyano, carboxyl, methoxycarbonyl, hydroxyl, hydroxymethyl, trifluoromethoxy, amino, N-methylamino, N,N-dimethylamino, N-ethylamino, N,N-dipropylamino, N-butylamino, N-methyl-N-ethylamino, nitro, methoxymethyl, methylsulfinyl, fluoro, chloro, bromo, methoxy, ethoxy, propoxy, n-butoxy, pentoxy, and methylthio; wherein $R^2$ is amino; and wherein $R^3$ is a radical selected from oxo, cyano, carboxyl, methoxycarbonyl, ethoxycarbonyl, carboxypropyl, carboxymethyl, carboxyethyl, cyanomethyl, fluoro, chloro, bromo, methyl, ethyl, isopropyl, butyl, tertbutyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, methoxy, ethoxy, propoxy, n-butoxy, pentoxy, cyclohexyl, phenyl, hydroxylmethyl, hydroxylpropyl, benzyl, formyl, phenylcarbonyl, methoxymethyl, furylmethyloxy, aminocarbonyl, N-methylaminocarbonyl, N,N-dimethylaminocarbonyl, N,N-dimethylamino, N-ethylamino, N,N-dipropylamino, N-butylamino, N-methyl-N-ethylamino, aminomethyl, N,N-dimethylaminomethyl, N-methyl-N-ethylaminomethyl, benzyloxy, and phenyloxy; or a pharmaceutically-acceptable salt thereof.

6. The method of claim 5 wherein the cyclooxygenase-2 inhibitor is selected from compounds, their prodrugs and their pharmaceutically-acceptable salts, of the group consisting of 4-[5-(4-chlorophenyl)-3-(trifluoromethyl)-1H-pyrazol-1-yl]benzenesulfonamide;

4-[5-(4-methylphenyl)-3-(trifluoromethyl)-1H-pyrazol-1-yl]benzenesulfonamide; and 4-[5-(3-fluoro-4-methoxyphenyl)-3-(difluoromethyl)-1H-pyrazol-1-yl]benzenesulfonamide.

* * * * *